United States Patent [19]

First et al.

[11] Patent Number: 5,213,979
[45] Date of Patent: May 25, 1993

[54] IN VITRO CULTURE OF BOVINE EMBRYOS

[75] Inventors: Neal L. First, Madison; Willard Eyestone, Verona, both of Wis.

[73] Assignee: W. R. Grace & Co.-Conn., New York, N.Y.

[21] Appl. No.: 139,887

[22] Filed: Dec. 30, 1987

[51] Int. Cl.$^5$ .............................................. C12N 5/00
[52] U.S. Cl. ............................ 435/240.2; 435/240.3; 435/240.25
[58] Field of Search ............. 435/240.2, 240.3, 240.25; 800/1

[56] References Cited

PUBLICATIONS

Eyestone et al., Thermogenology 27(1):228 (1987).
Freshney, "Culture of Animal Cells", Alan R. Liss, Inc., New York, (1983), pp. 78, 7, 106-110, 113-116.
Thibault, "La Culture In Vitro de L'Oeuf de Fache", Annls. Biochim. Biophys., vol. 6, pp. 159-164 (1966).
Camous, et al., "Cleavage Beyond the Block Stage and Survival After Transfer of Early Bovine Embryos Cultures with Trophoblastic Vesicles", J. Reprod. Fert., vol. 72, pp. 479-485 (1984).
Eyestone, et al., "Culture of One-and Two- Cell Bovine Embryos to the Blastocyst Stage in the Ovine Oviduct", Theriogenology, vol. 28, pp. 1-7 (1987).
Wright, et al., "Aspects of In Vitro Fertilization and Embryo Culture in Domestic Animals", J. Animal Science, vol. 53, No. 3, pp. 702-729 (1981).
Tervit, (H. R.), et al., "Successful Culture In Vitro of Sheep and Cattle Ova", J. Reprod. Fert., vol. 30, pp. 493-497 (1972).
Wright, et al., "Successful Culture In Vitro of Bovine Embryos to the Blastocyst Stage", Biol. Repr., vol. 14, pp. 157-162 (1976).
Rexroad, et al., "Co-culture of Sheep Ova and Cells from Sheep Oviduct", Theriogenology, vol. 25, p. 187 (1986).
Gandolfi, et al., "Role of Somatic Cells in the Long Term Culture of Ovine Embryos," Society for the Study of Fertility-Annual Conference, Abstract 111 (1986).

Primary Examiner—Jasemine C. Chambers
Attorney, Agent, or Firm—Vanessa L. Appleby; Jill H. Krafte

[57] ABSTRACT

The disclosure herein describes a bovine embryo culture medium which includes epithelial cells from the oviduct of a donor animal. Additionally, a process for maturing immature bovine oocytes in an in vitro bovine culture medium containing epithelial cells from a donor oviduct is described. As an alternative to co-culture of the embryos with the epithelial cells, it is described how a culture medium can be conditioned for the culture of bovine embryos by the culture of epithelial cells therein which are later removed.

36 Claims, No Drawings

IN VITRO CULTURE OF BOVINE EMBRYOS

FIELD OF THE INVENTION

The present invention is generally directed to the in vitro culture of bovine embryos. The present invention is specifically directed to a process for culturing bovine embryos in an in vitro culture medium containing either epithelial cells from a donor oviduct or supernatant from an epithelial cell culture.

DESCRIPTION OF THE PRIOR ART

Advanced genetic improvement and selection techniques continue to be sought in the field of animal husbandry. With specific reference to dairy cattle, for example, significant increases in milk production have been made with the wide scale use of genetically superior sires and artificial insemination. Dairy cows today produce nearly twice as much milk as they did thirty years ago.

It has now become an accepted practice to transplant embryos in cattle to aid in the production of genetically superior stock. One-cell fertilized eggs or pre-implantation embryos are generally obtained from mature female animals by non-surgical means which will preserve the health of the cells. The fertilized egg or embryo (containing the male and female pronuclei) undergoes syngamy (the union of the male and female pronuclei to form a zygote nucleus), followed by a series of cell divisions. As the embryo undergoes a series of mitotic divisions, it develops through the morula stage to the blastocyst stage where tissue differentiation and specialization occur. Ultimately, this leads to the formation of the fetus and placenta, which become implanted in the uterine wall.

Many techniques currently are under development for use in improving dissemination of genetically superior animals, such as embryo cloning, embryo transplantation, and the genetic transformation of embryonic tissues. These techniques require the culturing and manipulation of embryos in vitro. Workers developing these techniques most often begin with embryos obtained from superovulated animals.

Once the embryo has been obtained, it is a normal practice to culture the embryo in vivo in the ligated oviduct of a cow, sheep or rabbit until the embryo matures to the blastocyst stage. This surrogate oviduct system has allowed maturation of bovine embryos through a developmental block which previously has occurred prior to the blastocyst stage. While this procedure is effective, it is cumbersome and expensive. In addition, it requires the surgical ligation of the animal whose oviduct is to be used as the host and often sacrifice of the animal. Once the embryo has matured to the blastocyst stage, it is then recovered for the genetic manipulation, cloning, implantation, or whatever manipulation is intended for it, after which it is placed back into the reproductive tract of a recipient surrogate mother.

For successful commercial use of techniques such as genetic engineering or cloning, it must be possible to mature a single-cell embryo in vitro to the morula or blastocyst stage before it can be non-surgically transferred into a surrogate recipient mother to produce a pregnancy. However, bovine embryos encounter a block to in vitro bovine embryonic development at the 8- to 16-cell stage. Thibault, "La Culture *In Vitro* de L'Oeuf de Vache", *Annls. Biochim. Biophys.*, Vol. 6, pp. 159–164 (1966), Camous, et al., "Cleavage Beyond the Block Stage and Survival After Transfer of Early Bovine Embryos Cultured with Trophoblastic Vesicles", *J. Reprod. Fert.*, Vol. 72, pp. 479–485 (1984). Numerous efforts have been made to overcome this block to in vitro embryo maturation. As noted above, early stage embryos have been matured in a sheep oviduct. Eyestone, et al., "Culture of One- and Two-Cell Bovine Embryos to the Blastocyst Stage in the Ovine Oviduct", *Theriogenology*, Vol. 28, pp. 1–7 (1987), reported that ligated ovine oviducts would support development of ovine embryos from the 1-cell to blastocyst stage. Pregnancies and live calves were produced after transfer of cultured embryos to recipient heifers. Cultures of 1- and 2-cell embryos in the oviducts of intact cycling, ovariectomized and anestrous ewes produced morphologically normal morulae and blastocysts followed by pregnancies in recipient heifers, suggesting that ovarian activity was not required for normal embryo development in the oviduct.

These results suggest that there is a stage in bovine embryonic development, perhaps the 5- to 8-cell stage, which is a period of particular sensitivity to in vitro conditions. Therefore, it is likely that an important, environmentally sensitive event occurs around the 8-cell stage of embryonic development. Exposure of embryos to suboptimal conditions during this period may prevent the normal occurrence of this event, thus blocking further development.

It has been a goal of researchers to find a reliable in vitro culture system which will allow development of early bovine embryos to blastocyst stage. Such a development would effectively replace the surrogate oviduct system by an in vitro culture system and would greatly facilitate embryo manipulation procedures. The lack of a reliable in vitro culture system for early bovine embryos has hampered studies of early development and the application of these manipulation procedures.

Since 1949, efforts to develop fully-defined or semi-defined, i.e., containing biological fluids, culture systems for development of 1-cell bovine embryos to the blastocyst stage have been largely unsuccessful. Wright, et al., "Aspects of In Vitro Fertilization and Embryo Culture in Domestic Animals", *J. Animal Science*, Vol. 53, No. 3, pp. 702–729 (1981), except for occasional and apparently unrepeatable reports, Tervit, (H.R.), et al., "Successful Culture In Vitro of Sheep and Cattle Ova", *J. Reprod. Fert.*, Vol. 30, pp. 493–497 (1972). By contrast, later stage embryos, past the stage of the developmental block, have been cultured in vitro. Wright, et al., "Successful Culture In Vitro of Bovine Embryos to the Blastocyst Stage", *Biol. Repr.*, Vol. 14, pp. 157–162 (1976).

It has been reported by Rexroad, et al., "Co-culture of Sheep Ova and Cells from Sheep Oviduct", *Theriogenology*, Vol. 25, page 187 (1986), that the culture of 1-cell ovine embryos for 24 hours on monolayers of oviductal epithelium increases the proportion of embryos developing to the blastocyst stage upon transfer back to the sheep, compared with 1-celled embryos cultured 24 hours in Hams F-10+10% fetal calf serum culture medium. Gandolfi, et al., "Role of Somatic Cells in the Long Term Culture of Ovine Embryos," *Society for the Study of Fertility-Annual Conference*, Abstract 111 (1986), reported that freshly fertilized ovine embryos co-cultured on a feeder-layer of ovine oviductal cells developed to the blastocyst stage in vitro.

SUMMARY OF THE INVENTION

It is thus an object of the present invention to develop a in vitro bovine embryo culture system.

It is further an object of the present invention to create a complete in vitro culture system which develops a 1-cell bovine embryo to the blastocyst stage.

It is still further an object of the present invention to increase the proportion of 1-cell embryos cleaving beyond the 8- to 16-cell "block" in an in vitro cell culture system.

It is also an object of the present invention to create a method for effectively developing embryos in vitro from the fertilization stage to transferable blastocysts.

These and other objects will become more apparent from the following description of the present invention which is directed to a method for preparing an in vitro bovine culture system comprising preparing a culture medium containing either cells of fresh epithelial tissue or the supernatant or exudate from a culture of those cells and adding the bovine embryos. For purposes of the present invention, the terms "epithelial cells", "epithelial tissue", "epithelial layer", "epithelia" and "epithelium" all relate to the first few layers of cells found on the interior surface of the oviductal lumen.

The epithelial cells may be prepared by stripping epithelial tissue from the oviduct of a donor animal, removing non-cellular matter from the tissue leaving only dispersed epithelial cells, and placing the epithelial cells in a suitable culture medium known to the art. Cells may either remain in suspended or dispersed condition or may form a layer, preferably a monolayer, on the bottom of the cell culture dish. The epithelial cells may then either remain in the culture after the embryos are added, or alternatively, may be removed from the culture medium after the medium is conditioned by their presence. The embryos are then placed into the culture dish and allowed to mature in vitro through the 8- to 16-cell developmental block to the late morula or early blastocyst stage, i.e., to embryos of 40–60 cells. The method of the present invention results in the complete in vitro development from a 1-cell bovine embryo to the blastocyst stage. In fact, when combined with available in vitro fertilization techniques, it is now possible to fertilize and culture an embryo to the blastocyst stage completely in vitro.

The use of oviductal epithelial cells is superior to other types of cells, such as follicular cells (cells which develop from in or around an ovarian follicle) and trophoblastic vesicles (embryonic cells which attach to the uterine wall and function in the nutrition and implantation of the embryo). In addition, unlike follicular cells and trophoblastic vesicles, epithelial cells are conveniently obtainable from oviducts at the slaughter house or, after embryo recovery, by salpingectomy.

The co-culture of early bovine embryos with epithelial cells or with conditioned media according to the present invention improves the development of the embryos relative to culturing in standard culture medium alone. Although the reasons for this improvement are not certain, it is believed that the epithelial cells may impart a beneficial or "conditioning" effect to the culture system which permits early embryos to develop through the 8- to 16-cell block to the late morula and blastocyst stages in vitro. Possible beneficial effects may involve the secretion of vital nutritional or regulatory substances by the oviductal cells or the removal of embryotoxic substance from the medium. In any event, it has also been discovered that cultivating epithelial cells in the embryo culture medium conditions the medium to successfully host maturing embryos, even after the epithelial cells themselves are removed from the medium.

Thus, the co-culture of the present invention provides an attractive and more economical alternative to cumbersome in vivo culture methods. The co-culture or culture conditioning systems of the present invention will aid in studies of the nutritional and metabolic requirements of the early bovine embryo and facilitate in the application of various embryo manipulation techniques. From a practical standpoint, the process of the present invention is very versatile in that researchers will now be able to observe and assess the development of the embryo up to the blastocyst stage.

DETAILED DESCRIPTION OF THE INVENTION

The present invention is specifically directed to the development of an in vitro bovine culture system involving the co-culture of bovine embryos with primary cultures of oviductal epithelia and a standard culture medium. The present invention is also directed to the conditioning of a standard culture medium by culturing oviductal epithelial cells in the medium. Using either co-cultivation or conditioned media, it is now possible to fertilize a bovine embryo in vitro and to culture it continuously in vitro until ready for implantation in a surrogate mother. This facilitates the processing and treatment of embryos, including techniques such as genetic transformation and cloning, by making stable culture of bovine embryos easier and more convenient than was heretofore possible.

The basic requirements of an in vitro bovine embryo culture system are that it be simple to care for and use, reliable and consistent, reproducibly defined, without complex biological components such as serum, capable of supporting development to a stage compatible with nonsurgical uterine transfer, and capable of producing embryos with the potential of producing normal offspring. The addition of epithelial cells to a standard culture medium advantageously produces a bovine embryo culture system which satisfies all of the above requirements. The conditioning of a standard culture medium by culture with epithelial cells also satisfies all of these requirements.

Epithelial Tissue

The epithelial tissue is obtained by stripping the epithelium from a donor oviduct. The term "stripping" defines a number of methods of removing the epithelium, including slitting the oviduct longitudinally and scraping the epithelial tissue, or alternatively, soaking the oviduct in a specific enzyme designed to remove the epithelial layer. It is, however, preferred to remove the epithelial tissue from the oviduct by scraping the outer wall of the oviduct with a hard flat object, such as the edge of a glass microscope slide, a blunt knife, or similar instrument. Scraping the outer wall of the oviduct loosens the cells within the oviduct. Then, by gently squeezing the oviductal tube from one end to the other, a mass of epithelial cell tissue will emerge from the tube.

A primary culture of epithelial cells includes epithelial cells directly from the oviduct of the donor animal in the natural state. This would be the most faithful copy of oviductal epithelial layers. Primary cultures of oviductal epithelial cells are distinguished from secondary cultures, which can be formed by resuspending the cells and allowing them to undergo mitosis or other reactions. While primary culture epithelial cells are preferred, secondary culture cells may also prove effective in the present invention depending on the conditions of culture.

As will be apparent from the experimental examples below, the precise source of the epithelial tissue within the oviduct is not critical. The epithelial tissue may be from anywhere along the oviduct from the uterotubal junction to the ostium abdominale. Typically the cells will be from the isthmus or the ampulla, or both.

It is preferred that the epithelial cells be removed from donor females during their period of estrus or metestrus. Estrus can generally be determined by the presence of 1.5 to 2.0 millimeter (mm) diameter ovarian follicles, the presence of a regressing corpus luteum (CL) or the absence of an active CL, and the presence of copious amounts of cervical mucous. The oviductal tissue is obtained from estrual reproductive tracts in order to approximate synchrony of cycle stage between the oviduct donor and the embryo donor. Estrus and metestrus epithelial cells are preferred since it is only at estrus and metestrus that the cycle stage of a dissected ovary can be easily determined. Epithelial cells from oviduct tissue at other stages may also be effective.

Culture Medium

The embryo cells are preferably placed in an animal cell culture medium normally appropriate for maintaining the health and viability of animal cells. The preferred culture medium for a given application, e.g., for cells of a particular species and a particular development stage, will be known to one skilled in the art. Examples of known culture media which may be used for the purpose of the present invention include Ham's F-10+10% fetal calf serum (Ham's), Tissue Culture Medium-199+10% fetal calf serum (TCM-199), Tyrode's-Albumin-Lactate-Pyruvate (TALP), Dulbecco's Phosphate Buffered Saline (DPBS), Eagle's and Whitten's media, or any other media compatable with the continued viability of the bovine embryos. These listed media, their components and their methods of use are well known to those skilled in this art, as are a variety of other media. A medium will be considered suitable for the present invention if it is known to maintain embryonic cells and other animal cells in culture in a healthy and viable condition notwithstanding the fact that such a medium alone is insufficient to culture a bovine embryo past the block at the 8 to 16 cell stage.

Medium Conditioning

The culture medium may be conditioned for the culture of embryos by culture of epithelial cells in that medium, followed by removal of the epithelial cells prior to embryo introduction. While 20 hours of culture of the epithelial cells in the medium has been found sufficient to condition the medium for embryo development, it is to be understood that wide variations in this time period are possible, depending on type of medium, concentration and vitality of epithelial cells and similar factors. The parameters of the conditioning step can be readily determined for the selected media and conditions. The epithelial cells may be completely removed from the medium, by centrifugation, filtration or other technique prior to introducing the embryos to the medium. It is believed that the agent responsible for the conditioning is a embryotrophic factor exuded into the medium by the epithelial cells, and such separation techniques leave the factor in the medium. It may also be possible to separately synthesize or generate the embryotrophic factor and add it to the medium directly.

Source of Embryos

One through eight cell stage embryos and later stage bovine embryos obtained from the oviducts of superovulated or non-superovulated cows or heifers at 36 to 108 hours after the onset of estrus are preferred. The donor animals are synchronized with two injections (2cc) of chloprostenol sodium ("Estrumate", registered TM of Mills Laboratory, Shawnee, Kansas) and superovulated with a four day treatment of 40 mg FSH-P (Schering Corporation, Omaha, Nebr.). The donor embryos are most easily obtained by flushing from nonsurgically recovered oviducts or are nonsurgically flushed from the uterus in manners known to the art, but may also be obtained surgically.

The process for developing embryos past the in vitro "block" stage is now illustrated by the following examples. These examples are not meant to limit the invention described herein except as defined by the appended claims.

EXAMPLE 1

Example 1 was designed to test the advantages of adding epithelial cells to a culture medium. Bovine oviducts were obtained from an abattoir (slaughterhouse) and transported to the laboratory on ice. Oviducts were trimmed free of connective tissue to permit complete straightening of the oviduct. The epithelial cells were obtained by tissues stripped from oviducts by external scraping with a glass slide, starting at the isthmus and progressing toward the ampulla. The resulting mass of mucosal cells was expelled from the lumen of the oviduct and washed 5 times in 40 ml. modified Tyrode's solution. Bavister, B., et al. "Development of Preimplantation Embryos of the Golden Hamster in a Defined Culture Medium", *Biol. Reprod.*, Vol. 28, pp. 235–247 (1983). The final pellet was resuspended in Ham's medium to a concentration of 1 oviduct equivalent (the mass of cells obtained from a single oviduct) per 50 ml. medium. The tissue mass was then centrifuged in order to gently force the tissue mass to the bottom of the tube. The culture medium was again washed several times in order to wash away dead cells and non-cellular debris.

The clean epithelial cells were then added to a triple enzyme solution for approximately 90 minutes. The triple enzyme solution contained the following enzymes' 1) 200 units/ml. collagenase (Sigma Chemical Co. Type V) to rid the tissue of collagen which tends to bind the cells together; 2) 0.1% v/v trypsin (Sigma Chemical Co. Type III) to digest and remove the dead cells; and 3) 80 units/ml. deoxyribonuclease II (Sigma) to remove DNA released by dead cells. The enzymes were dissolved in $Ca^{++}$-$Mg^{++}$ free phosphate-buffered saline (0.05M, pH 7.3) containing 0.2 mg/ml. EDTA. The tissue was incubated for 45 min at 4° C., then at 37° C. for an additional 45 min. After incubation, the tissue was vigorously pipetted up and down in a pasteur pipette for 30 seconds to aid in tissue breakdown. The tissue was washed three more times in 15 ml. TCM-199.

The cell suspension was then resuspended in Ham's medium in order to terminate the trypsin activity, recentrifuged and rewashed to remove any remaining enzymes, and resuspended in Ham's medium. The cells were stained with 0.4% trypan blue and counted on a hemacytometer. After counting, the cells were resuspended in Ham's medium to a concentration of $1 \times 10^6$ live cells per ml.

Bovine embryos were fertilized in vivo and in vitro and collected. Embryos were assigned randomly to be co-cultured with oviduct tissue or cultured in Ham's medium alone. Ham's medium was used as a control. The embryos were added to the medium and observed every 24 hours. All cultures were terminated at a time equivalent to 7 days post-donor estrus. Final developmental state was noted and the proportion developing to late morula or blastocyst recorded. The number of nuclei per embryo was determined in some embryos after staining with Hoechst 33342 flourescent stain (2-[2-(4-ethoxyphenyl)-6-benzimidazoyl]-6-(1-ethyl-4-piperazyl)-benzimidazole) according to methods described in Critser, et al., "Use of a Fluorescent Stain for Visualization of Nuclear Material in Living Oocytes and Early Embryos", *Stain Technol.*, Vol. 61, pp. 1-5 (1986). The results are presented in Table 1.

TABLE 1

Proportion of Embryos Cleaving Beyond the 16-Cell Stage

| | Fertilized[a] In Vivo (%) | Fertilized[b] In Vitro (%) | Total (%) |
|---|---|---|---|
| Co-culture Embryos[d]/total | 41/63[c](65) | 7/13(54) | 48/76(63) |
| Control Embryos[d]/total | 0/17(0) | 0/11(0) | 0/28(0) |

[a]Initial embryo stages ranged from 1-8 cells.
[b]Initial embryo stages ranged from 1-2 cells.
[c]24 embryos developed to late morula or blastocyst.
[d]Embryos obtained at greater than 16-cell stage.

The results indicate that oviductal cells exert a positive effect on embryo development through the 8- to 16-cell stage where development by in vitro culture has previously been blocked.

EXAMPLE 2

This example compared the development of bovine embryo cells in a co-culture system of epithelial cells and Ham's medium with development in a control system of Ham's medium without epithelial cells. The epithelial cell cultures were prepared according to the methods described in Example 1. The epithelial cells were washed five times in 50 ml. of Tyrode's Hepes medium plus 3% bovine serum albumin, resuspended in Ham's medium at a rate of 1 oviduct equivalent per 100 ml. and pipeted into 24-well culture plates (1 ml/well). Control wells contained 1 ml. Ham's medium. Embryos (5- to 8-cell) obtained from superovulated heifers killed 48-72 hours post-estrus were co-cultured with oviductal epithelium or were cultured in the control Ham's medium. The cultures were placed in a humidified atmosphere of 5% $CO_2$ in air at 37° C. The results are presented below in Table 2.

TABLE 2

Development of Embryos Cultured in Ham's Medium or Co-Cultured With Oviductal Epithelium

| Culture Media | No. Late Morulae or Blastocysts/ Total | Nuclei/Embryo (X ± SD) |
|---|---|---|
| Control | 0/27 | 13.0 ± 2.65 |

TABLE 2-continued

| Co-Cultured | 38/82 | 48.3 ± 11.79 |
|---|---|---|

The results indicate that co-culturing bovine embryos with bovine oviductal tissue suspensions increased the proportion of embryos developing into late morula or blastocyst stage compared to a culture of bovine embryos in Ham's medium alone. None of the control embryos cleaved beyond the 8-16-cell stage.

EXAMPLE 3

Example 3 was designed to determine whether oviductal cell monolayers would support development of bovine embryos. Bovine oviducts from estrual and metestrual cows, obtained at slaughter or by salpingectomy, were processed to obtain mucosal tissue or according to the methods described in Example 1. The cells were added to 96 well culture plates at a density of $1 \times 10^6$ live cells/cm². Confluent monolayers formed after 48 hours. At this time, the original medium was removed and replaced with 150 microliters fresh TCM-199. Control wells were prepared by adding 150 microliters TCM-199 to empty wells. From this point on, 50 microliters of medium from both co-culture and control wells was replaced with 50 microliters fresh TCM-199 every day.

Bovine embryos at the 1-8 cell stage were obtained from the oviducts of superovulated heifers salpingectomized at 48-72 hours post-estrus. Embryos were distributed randomly for co-culture with oviduct monolayers or for culture in the TCM-199 control medium. Development was recorded at 24 hour intervals. The embryo cultures were terminated at a time equivalent to Day 7 post-donor estrus. The final developmental stage for each embryo was recorded. All embryos were stained according to the methods described in Example 1 and their nuclei counted. The proportion of embryos cleaving past the 8-16 cell block stage, i.e., greater than 16 nuclei per embryo, and the proportion developing to late morula or blastocyst stage were recorded. The results are presented below in Table 3.

TABLE 3

Development of Embryos Co-Cultured with Oviductal Cell Monolayers

| Treatment | No. Late Morula or Blastocyst Total (%) | No. Embryos Having > 16 cells Total (%) | Average Nuclei per Embryo |
|---|---|---|---|
| Co-Culture | 15/35(43) | 22/35(63) | 27.70 |
| Control | 0/37(0) | 2/37(0) | 8.83 |

The results of this experiment indicate that oviductal cells in a monolayer culture improve development to late morula and blastocyst stage compared to the TCM-199 medium control. Counts of embryonic nuclei indicated that cell number was greater after co-culture than after culture in control medium. Consistent with this result was the finding that the co-culture increased the proportion cleaving beyond the 16-cell stage.

EXAMPLE 4

Example 4 was designed to determine if the beneficial effect of the oviduct epithelial cells on the culture of bovine embryos persists in the medium after the epithelial cells were removed. In other words, this example tested whether the epithelial cells condition the medium, most probably either through the secretion or addition of a factor or the modification of a component of the medium, so that the conditioned medium would foster the growth of embryos past the 8-to-16 cell block. This example also demonstrates a successful complete in vitro culture from fertilization until blastocyst stage.

Oocytes were aspirated from 1-6 mm diameter follicles of ovaries obtained at slaughter and matured for 24 hours in TCM-199 supplemented with 10% heat-treated fetal calf serum, and with 50 micrograms gentamicin, 5 micrograms of ovine lutienizing hormone, 0.5 micrograms of ovine follicle stimulating hormone and 2 nanograms of estradiol per milliliter of medium. The oocytes were fertilized in vitro following the procedure of Parrish et al. "Bovine In Vitro Fertilization with Frozen Thawed Semen," Theriogenology, 25, pp. 591-600 (1986). Oviduct tissue was obtained from estrus and metestrus oviducts by the external scraping method described above. Suspension cultures of the epithelial cells were prepared by centrifuging the tissue at 100 times gravity for 4 minutes and resuspending the pellet in TCM-199 with 20% heat-treated fetal calf serum at a ratio of about 2:25 (volume:volume). Five milliliters of epithelial cell suspension were then added to a 40 milliliter culture flask and incubated for 20 hours at 39° C. in 5% $CO_2$ in air. Immediately prior to the start of embryo culture, the oviduct epithelial cell suspensions were diluted 1:1 (vol:vol) by fresh TCM-199. The conditioned media was then collected by centrifuging 2 milliliter aliquots of cell suspension in a microfuge for 2 minutes followed by drawing off the supernatant.

Sets of 60 mm culture dishes were then prepared for embryo culture by being supplied with 50 microliters of one of (1) conditioned media without epithelial cells, (2) epithelial cell co-culture, i.e medium with cells, or (3) with fresh TCM-199 alone as a control. The dishes were covered with 10 milliliter paraffin oil. The fertilized oocytes were removed from the fertilization medium after 18 hours, the cumulus was removed, and the embryos were transferred to one of the three media just described. After five days in culture, the embryos were examined for development past the 16 cell stage. Nuclei were stained with Hoechst 33342 to determine cell number in the embryos. The results are presented below in Table 4.

TABLE 4

| Development of Embryos in Conditioned Medium | | | |
|---|---|---|---|
| | TCM-199 Control (%) | Co-culture (%) | Conditioned Medium (%) |
| Number of >16-cell embryos/number of total embryos | 0/64(0%) | 15/67(22.4%) | 16/79(20.3%) |

Most of the embryos which cleaved past the 16 cell stage formed compact morulae or blastocysts. The percentage of embryos which developed past the 16 cell stage in both the co-culture and in the conditioned medium, as indicated above in Table 4, are comparable to the results observed in similarly prepared ova cultured in vivo in sheep oviducts. The results confirm that in vitro fertilized and in vitro matured bovine ova can be cultured into implantable embryos, past the 8-to-16 cell block in vitro in the presence of either oviduct epithelial cells or a medium conditioned by such cells. Since the data suggests that the positive influence of the oviductal cells on embryo cleavage ability is mediated by a diffusable factor or effect in the conditioned medium, and because the use of such a conditioned medium has clear practical advantages over a co-culture system, in general the use of conditioned media to culture embryos in vitro is likely to be the method of choice.

The above experiments indicate that the cultures of embryos either in a co-culture medium with epithelial tissue or in a conditioned medium provides an attractive alternative to the more cumbersome in vivo culture methods. Such embryo culture systems should aid in studies of the nutritional and metabolic requirements of early bovine embryos and facilitate in the application of various embryo manipulation techniques.

It is understood that the invention is not confined to the particular construction and arrangement herein described, but embraces such modified forms thereof as come within the scope of the following claims.

What is claimed is:

1. A method for preparing an in vitro bovine embryo culture system comprising:
   (a) obtaining fresh bovine epithelial cells from the oviduct of a donor animal, and;
   (b) adding the epithelial cells to an animal cell culture medium, which medium alone is insufficient to culture a bovine embryo past the 8 to 16 cell stage, and
   (c) culturing the epithelial cells in the culture medium so that the medium becomes capable of maintaining the health and viability of the bovine embryos through the 8 to 16 cells stage.

2. The method of claim 1 further comprising removing the epithelial cells from the medium after it has become conditioned by their presence.

3. The method of claim 1 wherein the culturing step includes co-culturing the epithelial cells with bovine embryos.

4. The method according to claim 1 wherein the epithelial cells are obtained by stripping the epithelial layer from an oviduct of a donor animal.

5. The method according to claim 4 wherein the oviduct is obtained from the estrual reproductive tract of an estrus or metestrus donor animal.

6. The method according to claim 4 wherein the epithelial cells are obtained from epithelial tissue in the oviduct at a location from the uterotubal junction to the ostium abdominale.

7. The method according to claim 6 wherein the epithelial cells are obtained from the ampulla of the oviduct.

8. The method according to claim 6 wherein the epithelial cells are obtained from the isthmus of the oviduct.

9. The method according to claim 3 wherein the epithelial cells are formed into a monolayer in the culture medium.

10. The method according to claim 1 wherein the epithelial cells are prepared for step (a) by washing epithelial tissue from the oviduct in a culture medium, enzymatically separating and removing the non-cellular material from the epithelial cells and rewashing the epithelial cells.

11. The method according to claim 10 wherein the method of enzymatically separating and removing the non-cellular material from the epithelial cell comprises adding the epithelial tissue to a solution of collagenase, trypsin and deoxyribonuclease enzymes.

12. The method according to claim 1 wherein the epithelial cells are dispersed in the culture medium to a density of at least about $1 \times 10^6$ live cells per centimeters squared.

13. The method according to claim 1 wherein the epithelial cells are dispersed in the culture medium to a density of about $1 \times 10^6$ live cells per centimeters squared.

14. The method according to claim 1 wherein the prepared culture medium is selected from the group consisting of Ham's medium, TCM-199, Dulbecco's Phosphate Buffered Saline medium, Tyrode's-Albumen-Lactate-Pyruvate medium, Whitten's medium and Eagle's medium.

15. The method according to claim 1 wherein the cells of the epithelial tissues are cultured in the prepared culture medium in a humidified atmosphere of 5% $CO_2$ in air at 37° C. for approximately 24 hours.

16. A method for the in vitro development of bovine embryos to the blastocyst stage, comprising adding bovine embryos to a culture system, wherein the culture system comprises:
   a) fresh bovine epithelial cells from the oviduct of a donor animal, and
   b) a culture medium capable of maintaining the health and viability of the bovine embryos in co-culture with the epithelial cells.

17. The method according to claim 16 wherein the epithelial cells are obtained by the steps of washing the epithelial tissue in a bovine culture medium, enzymatically separating and removing non-cellular material from the epithelial cells, and rewashing the epithelial cells.

18. The method according to claim 17 wherein the tissue and non-cellular material are enzymatically separated and removed from the epithelial cells in a triple-enzyme solution comprising collagenase, trypsin and deoxyribonuclease.

19. The method according to claim 16 wherein the epithelial cells are formed into a monolayer in the culture system.

20. The method according to claim 16 wherein the epithelial tissue is obtained by stripping the epithelial layer of the oviduct of a donor animal.

21. The method according to claim 20 wherein the oviduct is obtained from the reproductive tract of an estrus or metestrus donor animal.

22. The method according to claim 20 wherein the epithelial tissue is obtained from the oviduct at a location from the uterotubal junction to the ostium abdominale.

23. The method according to claim 16 wherein the cells are dispersed in a culture medium to a density of at least about $1 \times 10^6$ live cells per centimeters squared.

24. The method according to claim 16 wherein the cells are dispersed in a culture medium to a density of about $1 \times 10^6$ live cells per centimeters squared.

25. The method according to claim 16 wherein the prepared culture medium is selected from the group consisting of Ham's medium, TCM-199, Dulbecco's Phosphate Buffered Saline medium, Tyrode's-Albumen-Lactate-Pyruvate medium, Eagle's medium and Whitten's medium.

26. The method according to claim 16 wherein the cells of the epithelial tissues are cultured in a humidified atmosphere of 5% $CO_2$ in air at 37° C. or 39° C. for approximately 24 hours.

27. The method according to claim 16 further comprising maintaining the embryos in the culture system to the blastocyst stage.

28. A method for the in vitro culture of bovine embryos comprising the steps of:
   (a) obtaining epithelial cells from the oviduct of a donor animal,
   (b) adding the epithelial cells to an animal cell culture medium;
   (c) culturing the epithelial cells in the medium for a time sufficient to condition the medium for the culture of bovine embryos;
   (d) removing the epithelial cells from the conditioned medium; and
   (e) culturing bovine embryos in the conditioned medium to the blastocyst stage.

29. A method as claimed in claim 28 wherein the epithelial cells are obtained by stripping the epithelial layer of the oviduct of a donor animal.

30. The method according to claim 28 wherein after step (a) the epithelial cells are prepared by washing in a culture medium, enzymatically separating from non-cellular material, and rewashing.

31. The method according to claim 28 wherein the culture medium is selected from the group consisting of Ham's medium, TCM-199, Dulbecco's Phosphate Buffered Saline medium, Tyrode's-Albumin-Lactate-Pyruvate medium, Whitten's medium, and Eagle's medium.

32. The method according to claim 28 wherein step (d) is performed by centrifugation.

33. The method according to claim 28 wherein the bovine embryos are bovine ova which have been fertilized in vitro.

34. The method of claim 1 wherein the epithelial cells are cultured in suspension.

35. The method of claim 16 wherein the epithelial cells are cultured in suspension.

36. The method of claim 28 wherein the epithelial cells are cultured in suspension.

* * * * *

UNITED STATES PATENT AND TRADEMARK OFFICE
CERTIFICATE OF CORRECTION

PATENT NO. : 5,213,979

DATED : May 25, 1993

INVENTOR(S) : Neal L. First, Willard Eyestone

It is certified that error appears in the above-identified patent and that said Letters Patent is hereby corrected as shown below:

Claim 28, column 12, line 19:  After "obtaining" insert --bovine--.

Signed and Sealed this

Fourth Day of January, 1994

Attest:

BRUCE LEHMAN

Attesting Officer   Commissioner of Patents and Trademarks